US011214533B2

(12) United States Patent
Ku et al.

(10) Patent No.: US 11,214,533 B2
(45) Date of Patent: Jan. 4, 2022

(54) READILY BIODEGRADABLE ALKOXYLATE MIXTURES

(71) Applicant: Dow Global Technologies LLC, Midland, MI (US)

(72) Inventors: Sung-Yu Ku, Lake Jackson, TX (US); Wanglin Yu, Lake Jackson, TX (US); Christopher S. Letko, Lake Jackson, TX (US); Stephen W. King, Freeport, TX (US); Michael A. Brammer, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 154 days.

(21) Appl. No.: 16/621,831

(22) PCT Filed: Jun. 26, 2018

(86) PCT No.: PCT/US2018/039402
§ 371 (c)(1),
(2) Date: Dec. 12, 2019

(87) PCT Pub. No.: WO2019/005731
PCT Pub. Date: Jan. 3, 2019

(65) Prior Publication Data
US 2021/0139400 A1 May 13, 2021

Related U.S. Application Data

(60) Provisional application No. 62/526,092, filed on Jun. 28, 2017.

(51) Int. Cl.
*C11D 1/72* (2006.01)
*C11D 1/722* (2006.01)
*C11D 3/37* (2006.01)
*C07C 43/11* (2006.01)

(52) U.S. Cl.
CPC .............. *C07C 43/11* (2013.01); *C11D 1/722* (2013.01)

(58) Field of Classification Search
CPC ......... C11D 1/72; C11D 1/722; C11D 3/3707; C07C 43/11
See application file for complete search history.

(56) References Cited

U.S. PATENT DOCUMENTS

| 6,482,972 | B1 | 11/2002 | Bahrmann et al. |
| 6,602,823 | B1 | 8/2003 | Rochling et al. |
| 7,419,552 | B2 | 9/2008 | Ruland et al. |
| 2011/0098492 | A1* | 4/2011 | Varineau ................ C11D 1/722 549/554 |
| 2011/0319669 | A1 | 12/2011 | Yu et al. |

FOREIGN PATENT DOCUMENTS

| WO | 2009088778 | 7/2009 |
| WO | 2009155187 | 12/2009 |
| WO | 2016048764 | 3/2016 |

OTHER PUBLICATIONS

Yongchun, et al., "Properties and application of textile finishing agent", China Textile Publishing House, pp. 133-134, (1999) (4 gs) Original Copy Only; Translation Not Available.
Jutao, et al., "Dyeing and finishing auxiliaries and their applications", China Textile Publishing House, pp. 94-95, (2000) (4 pgs) Original Copy Only; Translation Not Available.
International Search Report & Written Opinion for related PCT Application, PCT/US2018/039402, dated Sep. 14, 2018 (11 pgs).
International Preliminary Report on Patentability for related PCT Application, PCT/US2018/039402, dated Jan. 9, 2020.

* cited by examiner

*Primary Examiner* — Brian P Mruk
(74) *Attorney, Agent, or Firm* — Brooks, Cameron & Huebsch, PLLC

(57) ABSTRACT

A mixture of octanols, nonanols and decanols is useful for the preparation of alkoxylates, which alkoxylates may be used as surfactants, which surfactants have surprisingly good biodegradability.

9 Claims, No Drawings

READILY BIODEGRADABLE ALKOXYLATE MIXTURES

This application is a National Stage Application under 35 U.S.C. § 371 of International Application Number PCT/US2018/039402, filed Jun. 26, 2018 and published as WO 2019/005731 on Jan. 3, 2019, which claims the benefit to U.S. Provisional Application 62/526,092, filed Jun. 28, 2017, the entire contents of which are incorporated herein by reference in its entirety.

FIELD

This disclosure relates to compounds that are useful as biodegradable surfactants.

BACKGROUND

Driven by regulations and increasingly growing environment and sustainability responsibilities, there is a strong demand for improved surfactants that are useful for different applications and that, at the same time, display favorable biodegradability and aquatic toxicity profiles.

2-Ethylhexanol (2-EH) is a commercially available alcohol that is useful as a solvent and for incorporation into plasticizers. However, for use as a hydrophobe in the preparation of surfactants, the number of carbon atoms in 2-EH is too small to provide sufficient hydrophobicity.

However, if propylene oxide (PO) or/and butylene oxide (BO) is added via propoxylation or butoxylation to the hydroxyl group of 2-EH (hereinafter referred to as PO-/BO-adducted 2-EH or PO/BO adducts of 2-EH), the ethoxylated nonionic surfactants of PO/BO-adducted 2-EH demonstrate unique performance advantages, including superior cleaning efficiency for hard surface cleaning, great adjuvancy in agrochemical formulations, excellent low foaming properties, and a high dissolution rate in water. It is believed the PO or BO block that is directly attached to the 2-EH hydroxyl group is at least partially responsible for these performance advantages. However, the PO or BO block compromises the biodegradability of the resulting surfactants. In order to pass the "readily biodegradability" criteria (as measured by the OECD 301 methods), the adducted PO block size should be less than about 6 PO repeat units. "Enhanced Cleaning through Hydrophobe Modification of Alcohols using Alkylene Oxides" by Varineau, P.; Doneva, T.; Argenton, A.; Thompson, K.; Weber, K.; Cameron, P.; Madrigal, L.; MacKinnon, J.; and Alam, F., from *Communicaciones presentadas a las Jornadas del Comite Espanol de la Detergencia* (2009) 39, 21-31. The limited PO block size required to maintain ready biodegradability results in a shortcoming for the subsequently ethoxylated surfactants of the PO-adducts of 2-EH, namely undesirably high critical micelle concentrations (CMCs). The ethoxylated surfactants of 5PO-adducted 2-EH exhibit CMC values close to 1000 ppm when the surfactants are synthesized to have a cloud point in water in the range of 20-70° C., which is one of the most useful cloud point ranges for many end-use applications. High CMC values may cause a surfactant to be less effective at low concentrations in many formulations and applications.

2-Propylheptanol (2-PH) is another alcohol largely used as a solvent and for incorporating into plasticizers. 2-PH has also been used as a hydrophobe to produce surfactants. Compared to 2-EH, two more —$CH_2$— units in 2-PH affords more hydrophobicity and makes 2-PH a better hydrophobe compared to 2-EH. However, 2-PH ethoxylated surfactants also have high CMC values when they are synthesized to have a cloud point in water in the range of 20-70° C. For example, LUTENSOL XP-70 shows a CMC of around 900 ppm while its cloud point in water is close to 20° C. The use of PO to extend the hydrophobicity of 2-PH to lower the CMC of 2-PH derived surfactants and to pursue the performance advantages as seen in the PO-adducted 2-EH ethoxylated surfactants is limited due to the lack of ready biodegradability of the resulting surfactants. U.S. Pat. No. 7,5479,552 teaches that the addition of greater than 1 equivalent of PO to 2-PH causes the loss of ready biodegradability of the resulting surfactants. Therefore, the lack of ready biodegradability limits the use of PO-adducts of 2-PH to reduce the CMC of surfactants and to pursue the desired performance advantages.

It would be desirable to have an alkoxylate composition that is useful as a surfactant, is readily biodegradable, and that may have other improved properties compared to commercially available surfactants of similar composition.

SUMMARY

The composition of this disclosure is such a composition, and comprises an alkoxylate mixture comprising compounds of the following formula:

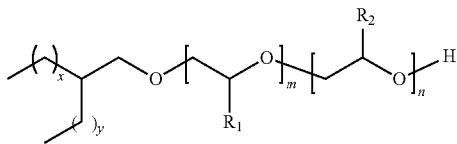

wherein R1 is methyl or ethyl, R2 is a hydrogen, methyl or ethyl group, x is 3 or 4, y is 1 or 2, m has an average value of from 1 to 15, and n has an average value of 0 to 40, with the proviso that the mixture includes a compound wherein x+y is 4, a compound wherein x+y is 5 and a compound wherein x+y is 6.

Surprisingly, the biodegradable composition of this disclosure may be useful as a surfactant and may have improved properties compared to commercially available surfactants of somewhat similar composition. For example, the composition may demonstrate ready biodegradability and excellent cleaning effectiveness with one or more of the following improved properties: low CMC values, a high dissolution rate in water, and/or a narrow gel range.

DETAILED DESCRIPTION

The alkoxylate mixture of this disclosure comprises a plurality of compounds of the following formula:

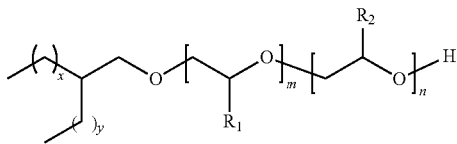

wherein R1 is either methyl or ethyl or a combination thereof, R2 is either hydrogen, methyl or ethyl or any combination thereof, x is 3 or 4, y is 1 or 2, m has an average value of from 1 to 15, and n has an average value of 0 to 40, with the proviso that the mixture includes a compound wherein x+y is 4, a compound wherein x+y is 5 and a compound wherein x+y is 6.

As used herein, the terms EO, PO and BO refer, respectively to ethylene oxide, propylene oxide and butylene oxide.

As used herein, the term "2-EH+5PO+6EO" refers to a compound that is initiated with 2-EH and has 5 moles of PO and 6 moles of EO added thereto. This convention is employed for similar compounds herein. See, e.g. Example 2.

It is understood that "m" and "n" represent average degrees of alkoxylation. Thus, m and n may be integers but need not be integers. Taken together, m and n establish a degree of alkoxylation in an oligomer distribution. It should be apparent that the order of m and n is block or random, e.g. the "m block" in Formula I may contain both PO and BO remnants, or may be pure PO or pure BO blocks. Similarly, the "n block" may be block or random units comprising remnants of EO, PO and/or BO. The terms "n block" and "m block" refer to the alkoxide remnants whose number is represented by n and m, respectively in the compound of Formula I.

As used herein, the terms "a," "an," "the," "at least one," and "one or more" are used interchangeably. The terms "comprises" and "includes" and variations thereof do not have a limiting meaning where these terms appear in the description and claims. Thus, for example, "a" material can be interpreted to mean "one or more" materials, and a composition that "includes" or "comprises" a material can be interpreted to mean that the composition includes things in addition to the material.

"Reaction medium" includes, but is not limited to, a liquid in which at least one reactant is at least partially soluble. Thus, for a given reaction, it is possible that all reactants are solubilized in the reaction medium, but it is also possible that the reactants form a suspension in the reaction medium. Other combinations are also possible.

As used herein, the term "N:I ratio" refers to the molar ratio of normal-aldehydes (N) to iso-aldehydes (I).

As used herein, the terms "C8-C10 alcohols" and "C8-C10 alcohol mixture" are used interchangeably and refer to a mixture of alcohols comprising 2-ethylhexanol (C8), 2-ethylheptanol (C9), 2-propylhexanol (C9) and 2-propylheptanol (C10).

As used herein the terms "C8-C10 enals" and "mixed C8-C10 enals" are used interchangeably and refer to a mixture comprising 2-ethylhexenal, 2-ethylhept-2-enal, 2-propyhex-2-enal and 2-propylheptenal.

Unless stated to the contrary, implicit from the context, or customary in the art, all parts and percentages are based on weight and all test methods are current as of the filing date of this disclosure.

The alkoxylates may be prepared by a process comprising the following steps. (1) conducting a cross aldol condensation of a mixture of butyraldehyde and valeraldehyde under reaction conditions sufficient to produce a corresponding mixture of enals; (2) hydrogenating the mixture of enals under reaction conditions sufficient to produce a mixture of alcohols; and (3) alkoxylating the mixture of alcohols under reaction conditions sufficient to produce the alkoxylate mixture.

In one embodiment, in the first step of the process for preparing the alkoxylate mixture, a cross aldol condensation of a mixture of butyraldehyde and valeraldehyde may be employed to produce a corresponding mixture of enals. The aldehydes employed for the cross aldol condensation comprise butyraldehyde and valeraldehyde. The butyraldehyde may be produced via the hydroformylation of propylene. The butyraldehyde may comprise a mixture of linear n-butyraldehyde and 2-methypropionaldehyde (also known as isobutyraldehyde). The ratio of n-butyraldehyde to isobutyraldehyde (N:I ratio) may vary from about 2:1 to about 200:1; preferably from about 7:1 to about 150:1; and more preferably from about 10:1 to 150:1. The manner in which the butyraldehyde is obtained is not a critical aspect of the current disclosure. Methods for the hydroformylation of propylene are known to the skilled person and typically comprise feeding propylene, carbon monoxide and hydrogen to one or more reactors containing a rhodium catalyst promoted by one or more phosphorous ligands. Details may be found, for example, in U.S. Pat. Nos. 4,148,830, 4,717,775 and 4,769,498.

The valeraldehyde may be produced via the hydroformylation of 1-butene or mixed butenes, such as Raffinate I or Raffinate II. The valeraldehyde may comprise a mixture of linear n-valeraldehyde and 2-methylbutyraldehyde (also known as isovaleraldehyde). The ratio of n-valeraldehyde to iso-valeraldehyde (N:I ratio) may be from about 2:1 to 500:1; preferably from about 20:1 to 200:1; and more preferably from about 30:1 to 200:1. The manner in which the valeraldehyde is obtained is not a critical aspect of the current disclosure. Methods for the hydroformylation of 1-butene and mixed butenes, e.g. Raffinate I and II, are known to the skilled person and typically comprise feeding 1-butene or mixed butenes, carbon monoxide and hydrogen to one or more reactors containing a rhodium catalyst promoted by one or more phosphorous ligands. Details may be found, for example, in WO 2010/003073.

In one embodiment, the enal mixture is prepared by the cross aldol condensation of butyraldehyde and valeraldehyde. The molar ratio of butyraldehyde to valeraldehyde employed may range from about 1:4 to 4:1; preferably from 1:2 to 2:1. In one embodiment, an equimolar mixture of butyraldehyde and valeraldehyde is utilized. The molar ratios of the enal products will vary based on the relative molar amounts of butyraldehyde and valeraldehyde employed. The major components of the enal mixture comprise 2-ethylhexenal, 2-ethylhept-2-enal, 2-propylhex-2-enal and 2-propylheptenal. In one embodiment, increasing the molar ratio of butyraldehyde to valeraldehyde will increase the amount of 2-ethylhexenal in the enal mixture. In another embodiment, increasing the molar ratio of valeraldehyde to butyraldehyde will increase the amount of 2-propylheptenal in the enal mixture. In a preferred embodiment, an equimolar mixture of butyraldehyde and valeraldehyde is employed to provide an enal mixture having a molar ratio of approximately 1:1:1:1 2-ethylhexenal, 2-ethylhept-2-enal, 2-propylhex-2-enal and 2-propylheptenal.

In one embodiment, the enal mixture comprises enals derived in part from the aldol condensation of the isoaldehyde starting materials. For example, in one embodiment the enal mixture comprises enals derived from the aldol condensation of isobutyraldehyde with n-butyraldehyde and/or n-valeraldehyde. In one embodiment, the enal mixture comprises enals derived from the aldol condensation of isovaleraldehyde with n-butyraldehyde and/or n-valeraldehyde. The total concentration of the enals derived from the isoaldehyde starting materials will vary depending on the N:I ratio of the butyraldehyde and valeraldehyde starting materials employed, and will range from about 1 to 15%, preferably from about 1 to 10%.

The conditions for conducting the cross aldol condensation are not critical to the disclosure, and typically comprise feeding the aldehydes to a stirred vessel containing a catalyst at elevated temperature. The catalyst may comprise an acid or base; for example aqueous sodium hydroxide is an effective, commonly used catalyst. Methods for aldol condensation are well known to those skilled in the art; see, for example, U.S. Pat. No. 5,434,313.

In one embodiment, in the second step of the process for the preparation of the alkoxide mixture, the enal mixture is hydrogenated to produce an alcohol mixture. The conditions of the hydrogenation are not critical to the current disclosure, and are known to the skilled person; see for example U.S. Pat. No. 4,960,960.

In one embodiment, an alcohol composition comprising at least one branched C8 alcohol, at least two branched C9 alcohols and at least one branched C10 alcohol is produced via a process comprising a mixed aldol condensation of butyraldehyde and valeraldehyde, followed by hydrogenation of the resulting enals. In one embodiment, the alcohol mixture has the same relative molar composition of C8:C9:C10 as the mixture of enals from the first process step. The mixture of alcohols may be used "as is" or it may be refined, e.g. by distillation, to produce a mixture of alcohols of a desired composition.

In one embodiment, the alcohol mixture comprises a desired mixture of the C8, C9 and C10 alcohols. In one embodiment, the alcohol composition comprises from 10 to 40 mole percent of a C8 alcohol, from 20 to 80 mole percent of C9 alcohols, and from 10 to 40 mole percent of a C10 alcohol, wherein the total percentage is 100. In one embodiment, the alcohol composition comprises from 20 to 30 mole percent of a C8 alcohol, from 40 to 60 mole percent of C9 alcohols, and from 20 to 30 mole percent of a C10 alcohol, wherein the total percentage is 100. In one embodiment, the molar ratio of C8:C9:C10 alcohols in the alcohol composition is nominally 1:2:1. In one embodiment, the C9 alcohol of the alcohol composition comprises 2 isomers, namely 2-ethylheptanol and 2-propylhexanol.

In one embodiment, the alcohol mixture is employed as the substrate for the preparation of the alkoxylate mixture of the disclosure.

In one embodiment, the alkoxylate mixture is prepared by the alkoxylation of the alcohol mixture. Alkoxylation processes may be carried out in the presence of acidic or alkaline catalysts, or a double metal cyanide catalyst as is well-known to those skilled in the art. It is preferred to use an alkaline catalyst, such as a hydroxide or alcoholate of sodium or potassium, including, for example, NaOH, KOH, sodium methoxide, potassium methoxide, sodium ethoxide and potassium ethoxide. Alkaline catalysts may be used in a concentration of from 0.05 percent to about 5 percent by weight, preferably about 0.1 percent to about 1 percent by weight, based on the weight of the reactants. Mixtures of catalysts may be employed.

In one embodiment, the alkoxylation is conducted in two stages. The "m block" is formed in the first stage and the "n block" is formed in the second stage. In one embodiment, only propylene oxide or only butylene oxide is employed as the alkylene oxide for the first alkoxylation. In one embodiment, both PO and BO are employed as the alkylene oxide for the first alkoxylation. The feed to the first alkoxylation stage may be conducted in a manner to form a random or block alkoxide segment. In one embodiment, the alcohol mixture is converted to form a nonionic surfactant via alkoxylation of the alcohol mixture with from 1 to about 15 moles of propylene oxide and/or BO. In one embodiment, no second stage is employed, i.e. n=0.

The first alkoxylated product may be further alkoxylated in the second alkoxylation stage by using one or more alkylene oxides to form a second alkoxylated product. Examples of the alkoxylates made via a second stage alkoxylation include those prepared by further alkoxylating the first alkoxylated product in a second stage with an alkylene oxide, namely ethylene oxide, propylene oxide, and/or butylene oxide, either alone or as a mixture of any 2 or all 3 of these alkylene oxides. The feed to the second alkoxylation stage may be conducted in such a manner as to form a random or block alkoxide segment.

The alkoxylate product may be a mixture of a first alkoxylate product wherein n is zero, and other alkoxylates wherein n is greater than zero, e.g. n has a positive nonzero value as stated elsewhere herein. In one embodiment, the alkoxylate mixture may contain from 1 to 50 wt. % of one or more first alkoxylate products, i.e. products of the first alkoxylation stage, and from 50 to 99 of other alkoxylates, e.g. one or more products of the second alkoxylation stage.

The addition of the alkylene oxide may, in one embodiment, be carried out under pressures from about 10 psig to about 200 psig, preferably from about 60 to about 100 psig. The temperature of alkoxylation may range from about 30° C. to about 200° C., preferably from about 100° C. to about 160° C. After completion of the oxide feed, the product is typically allowed to react until the residual oxide is less than about 10 ppm. After cooling the reactor to an appropriate temperature ranging from about 20° C. to 130° C., the residual catalyst may be left unneutralized, or neutralized (in the case of basic catalysts) with organic acids such as, for example, acetic, propionic, or citric acid. Alternatively, the product may be neutralized with inorganic acids, such as, for example, phosphoric acid or carbon dioxide. Residual catalyst may also be removed using ion exchange or by using an adsorption media, such as diatomaceous earth. In many nonlimiting embodiments the resulting alkoxylated material may be an effective surfactant.

In one embodiment, the alkoxylate mixture comprises compounds represented by the formula I:

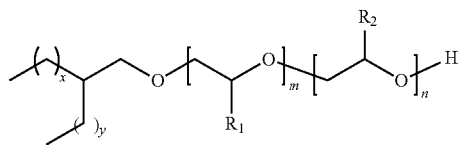

wherein R1 is either methyl or ethyl or a combination thereof, R2 is either hydrogen, methyl or ethyl or any combination thereof, x is 3 or 4, y is 1 or 2, m has an average value of from 1 to 15, and n has an average value of 0 to 40, with the proviso that the mixture includes a compound wherein x+y is 4, a compound wherein x+y is 5 and a compound wherein x+y is 6.

In some embodiments, m is from 1 to 15 or 1 to 5 or 3 to 5 or 3 to 10, and n is from 0 to 40 or 1 to 40 or 3 to 40 or 3 to 15. In one embodiment, R1 is either methyl or ethyl or a combination thereof. R2 is either hydrogen, methyl or ethyl or any combination thereof. In some embodiments, x is 3 or 4, y is 1 or 2, and m has an average value of from 1 to 15. In some embodiments, m is from 3 to 10 and n is from 1 to 40, or m is from 3 to 5 and n is from 3 to 40. In some embodiments, R1 is methyl, R2 is hydrogen, x is 3 or 4, y is 1 or 2, m has an average value of from 3 to 5, and n has an average value of 3 to 15. In some embodiments, R1 is methyl or ethyl, x is 3 or 4, y is 1 or 2, and m has an average value of from 1 to 15. In some embodiments, R1 is methyl, x is 3 or 4, y is 1 or 2, and m has an average value of from 3 to 5. In various embodiments, m is from 1 to 5, or from 3 to 5.

The alkoxylate mixture of this disclosure may be employed as a surfactant, either alone or with other surfactants. Applications of the surfactant of this disclosure may include a wide variety of formulations and products. These include, but are not limited to, uses in kitchen cleaners, cleaners for triglycerides, cross-linked triglycerides, or mixtures thereof, cleaners for mineral oil-type soils, hydrotropes for formula stabilization, surfactant for ultra-concentrate formulas, self-hydrotroping surfactants for enhanced formula stabilization with surfactant activity, general cleaners, pre-wash spotting agents, pre-wash concentrates, detergents, hard surface cleaning formulations, metal cleaning and metal working processes, textile and leather treatment processes, pulp and paper processes, paint and coating formulations, ink and adhesive formulations, emulsion polymerizations, agrochemical formulations, and oil and gas production.

SPECIFIC EMBODIMENTS

Preparation 1: Preparation of Mixed C8-C10 Enals Via a Cross Aldol Condensation The procedure is conducted in a mechanically stirred 10 gallon stainless steel reactor rated for high pressure service. Heating is supplied by circulating hot oil through an outer jacket; and the reactor temperature is monitored by a thermocouple in contact with the stirred reaction mixture.

A 2 wt. % aqueous sodium hydroxide solution (7723 g) is charged to the reactor and agitation is initiated at ambient temperature. A premixed solution of butyraldehyde (N:I ratio 10:1; 5273 g; 73 moles) and valeraldehyde (N:I ratio 45:1; 6284 g; 73 moles) is pumped into the reactor slowly over 15 minutes. The aldol condensation reaction is exothermic; thus, the temperature of the reaction mixture rises during this time from 20° C. to 44° C. Once the aldehyde addition is complete, heating is initiated, and the temperature of the reaction mixture is increased to 130° C. over the course of one hour and then is maintained at that temperature for an additional two hours. Then, the reactor is cooled and the biphasic reaction mixture is decanted. The organic (top) layer is analyzed on an Agilent 6890 GC using the conditions described in the following table:

| Inlet | 250° C. |
|---|---|
| Split Ratio | 200:1 |
| Detector Temperature (FID) | 300° C. |
| Column | DB-1 60 m × 0.32 mm; 1µ film |
| ISTD | Hexyl acetate |
| Total Run Time | 70 min |

| Oven Temperature (° C.) | Ramp (° C./min) | Hold Time (min) |
|---|---|---|
| 60 | 0 | 6 |
| 106 | 6 | — |
| 142 | 4 | — |
| 270 | 15 | 37 |

The analysis indicates four major products, namely a mixture of 2-ethylhexenal, 2-ethylhept-2-enal, 2-propyhex-2-enal and 2-propylheptenal at a molar ratio of 1.2:1.0:1.2:1.3. Two minor enal products attributed to condensation reactions of isobutyraldehyde with butyraldehyde and valeraldehyde respectively are also detected; the combined concentration of these two minor enal products is approximately 5 wt. %. The total concentration of unreacted butyraldehyde and valeraldehyde is approximately 2 wt. %, indicating nearly complete conversion.

Preparation 2: Hydrogenation of Mixed C8-C10 Enals

Initial catalyst loading: Twenty five grams of water wet Raney Ni 5887-200 is transferred into a Robinson-Mahoney basket and placed into a 1 liter reactor. Three "pressurization to 500 psia and venting" cycles of the reactor are conducted then 3 similar cycles with nitrogen, another three times with hydrogen, and the reactor is then purged with nitrogen to remove any water from the catalyst. Approximately 350 g of n-butanol is loaded to the reactor, is mixed at 300 rpm, and is drained to remove any fines. Catalyst washing with n-butanol is completed three times. An additional three pressurization to 500 psia and venting cycles are completed using hydrogen. The reactor is then left at 500 psia under hydrogen with a jacket temperature of 100° C. for 48-72 hours prior to the hydrogenation process.

The C8-C10 enals from the cross aldol reaction are loaded into a 500 mL shot tube in approximately 250 g increments at ambient temperature. Five nitrogen pressurization-venting-vacuum cycles are completed prior to addition of the enals to the reactor. The reaction is controlled at approximately 25° C. and 1000 rpm during the addition of the enals. Hydrogen pressure control is established and time zero is established at the time the temperature is ramped to the desired set point. The end of the reaction is defined by zero hydrogen being consumed from the 1 gallon hydrogen supply cylinder. At the conclusion of the run, the product is drained and filtered to remove Raney Nickel catalyst fines. The resulting mixture of C8-C10 alcohols is characterized by gas chromatography using a flame ionization detector (GC-FID) to obtain the alcohol compositions and ratios.

GC-FID is used to further characterize the isomeric composition of the C8-C10 alcohols. Four major alcohol isomers are identified in the GC-FID spectra, which includes four major components: 2-ethylhexanol (2-EH, a C8 alcohol, 21.6 area %), 2-ethylheptanol (C9-1, a C9 alcohol, 22.0 area %), 2-propylhexanol (C9-2, a C9 alcohol, 21.0 area %) and 2-propylheptanol (2-PH, a C10 alcohol, 28.9 area %). Less than 4 area % of two other isomers are from a branched C8 alcohol (2.7 area %) and a branched C9 alcohol (3.8 area %). The C9 alcohol isomers (C9-1 and C9-2), which are difficult to obtain using tedious prior art synthetic approaches, constitute 43 area % of the product mixture. Calculated product ratios using GC-FID data are found to correspond to a nominal C8:C9:C10 molar ratio of 1:2:1. The analytical data is summarized in Table 1.

TABLE 1

A summary of GC-MASS and GC-FID peak areas determined for the resulting mixture of C8-C10 alcohols.

| | FID Area % | Molar Ratio |
|---|---|---|
| 2-EH; C8 alcohol | 21.6 | 1.0 |
| C9-1 | 22.0 | 0.9 |
| C9-2 | 21.0 | 0.9 |
| 2-PH; C10 alcohol | 28.9 | 1.1 |

The reactions and the chemical structures of the starting materials and products as described in Preparation 1 and Preparation 2 are illustrated in Scheme 1:

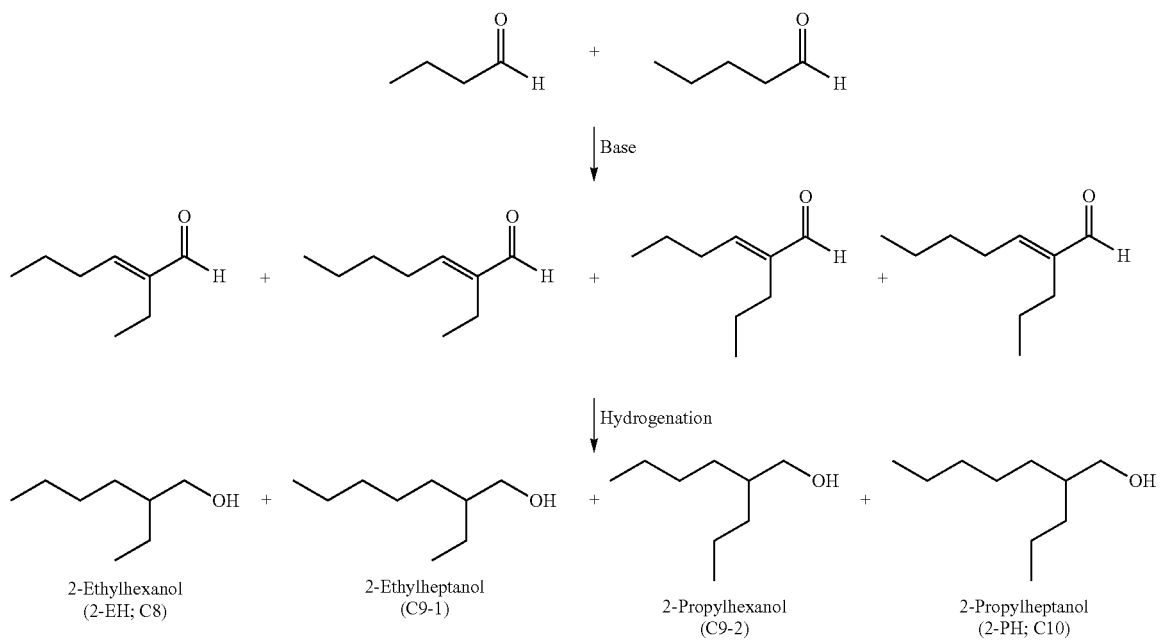

2-Ethylhexanol (2-EH; C8)  2-Ethylheptanol (C9-1)  2-Propylhexanol (C9-2)  2-Propylheptanol (2-PH; C10)

The C8-C10 alcohol mixture prepared via Preparation 1 and Preparation 2 is purified by distillation to remove impurities. The resulting purified mixture is employed in the alkoxylation reactions that follow.

Alkoxylation Equipment

Alkoxylation reactions are carried out in a 2 L 316 stainless steel conical bottom Parr reactor, model 4530, equipped with a ¼ hp magnetic drive agitator, 1500 watt (115V) Calrod electric heater, ¼ inch water-filled cooling coil, 1/16 inch dip tube for sampling, internal thermowell, ¼ inch rupture disc set at 1024 psig, ¼ inch relief valve set at 900 psig, an oxide addition line submerged below the liquid level, and a 2 inch diameter pitch-blade agitator. The oxide addition system consists of a 1 liter stainless steel addition cylinder, which is charged, is weighed, and is attached to the oxide load line.

The reactor system is controlled by a Siemens SIMATIC PCS7 process control system. Reaction temperatures are measured with Type K thermocouples, pressures are measured with Ashcroft pressure transducers, ball valves are operated with Swagelok pneumatic valve actuators, cooling water flow is controlled with ASCO electric valves, and oxide addition rates are controlled by a mass flow control system consisting of a Brooks Quantim® Coriolis mass flow controller (model QMBC3L1B2A1A1A1DH1C7A1DA) and a TESCOM back pressure regulator (model 44-1163-24-109A) that maintains a 100 psig pressure differential across the mass flow controller to afford steady flow rates.

Example 1: Alkoxylation of C8-C10 Alcohols: C8-C10+3PO

The 2 L Parr reactor is charged with 19.98 g (143 mmol) of C8-C10 the alcohol mixture of Preparation 2 and 0.1001 g of 85% potassium hydroxide powder. After a pressure check and a series of nitrogen purges, the mixture is warmed to 130° C. for the addition of 25.0 g (430 mmol) of propylene oxide at an addition rate of 1 g/min. The reaction product is held at 130° C. overnight, then is cooled and is unloaded to afford 40.82 g of a liquid. The liquid is mixed with 87 µL of acetic acid to neutralize the potassium hydroxide catalyst.

Example 2: Alkoxylation of C8-C10 Alcohols: C8-C10+3PO+3EO

The 2 L Parr reactor is charged with 19.93 g (143 mmol) of the C8-C10 alcohol mixture of Preparation 2 and 0.1045 g of 85% potassium hydroxide powder. After a pressure check and series of nitrogen purges, the mixture is warmed to 110° C. and the headspace purged for 15 minutes. A fine mist exits the vent. The mixture is warmed to 130° C. for the addition of 25.1 g (432 mmol) of propylene oxide at an addition rate of 1 g/min. After the addition is complete and the pressure stabilizes, 19.1 g (434 mmol) of ethylene oxide is added at a rate of 1 g/min. The reaction product is held at 130° C. overnight, then is cooled and is unloaded to afford 58.21 g of a liquid. The liquid is mixed with 90 µL of acetic acid to neutralize the potassium hydroxide catalyst.

Example 3: Alkoxylation of C8-C10 Alcohols: C8-C10+3PO+6EO

The 2 L Parr reactor is charged with 20.04 g (143 mmol) of the C8-C10 alcohol mixture of Preparation 2 and 0.0980 g of 85% potassium hydroxide powder. After a pressure check and series of nitrogen purges, the mixture is warmed to 130° C. for the addition of 25.0 g (430 mmol) of propylene oxide at an addition rate of 1 g/min. After the addition is complete and the pressure stabilizes, 37.3 g (847 mmol) of ethylene oxide is added at a rate of 1 g/min. The reaction product is held at 130° C. overnight, then is cooled and is unloaded to afford 78.85 g of a liquid. The liquid is mixed with 85 µL of acetic acid to neutralize the potassium hydroxide catalyst.

Example 4: Alkoxylation of C8-C10 Alcohols: C8-C10+3PO+9EO

The 2 L Parr reactor is charged with 19.95 g (143 mmol) of the C8-C10 alcohol mixture of Preparation 2 and 0.1082 g of 85% potassium hydroxide powder. After a pressure check and series of nitrogen purges, the mixture is warmed to 130° C. for the addition of 25.0 g (430 mmol) of propylene oxide at an addition rate of 1 g/min. After the addition is complete and the pressure stabilizes, 55.1 g (1250 mmol) of ethylene oxide is added at a rate of 1 g/min. The reaction product is held at 130° C. overnight, then is cooled and is unloaded to afford 96.73 g of a liquid. The liquid is mixed with 94 µL of acetic acid to neutralize the potassium hydroxide catalyst.

Example 5: Alkoxylation of C8-C10 Alcohols: C8-C10+5PO

The 2 L Parr reactor is charged with 49.95 g (348 mmol) of the C8-C10 alcohol mixture of Preparation 2 containing 0.61 wt. % KOH. After a pressure check and a series of nitrogen purges, the mixture is warmed to 130° C. for the addition of 101.2 g (1742 mmol) of propylene oxide at an addition rate of 1 g/min. The reaction product is held at 100° C. overnight, then is cooled and is unloaded to afford 142.89 g of a liquid. The liquid is mixed with 0.31 mL of acetic acid to neutralize the potassium hydroxide catalyst.

Example 6: Alkoxylation of C8-C10 Alcohols: C8-C10+5PO+5EO

The 2 L Parr reactor is charged with 50.22 g (349 mmol) of the C8-C10 alcohol mixture of Preparation 2 containing 0.61 wt. % KOH. After a pressure check and series of nitrogen purges, the mixture is warmed to 130° C. for the addition of 101.2 g (1742 mmol) of propylene oxide at an addition rate of 1 g/min. After the addition is complete and the pressure stabilizes, 76.7 g (1741 mmol) of ethylene oxide is added at a rate of 1 g/min. The reaction product is held at 130° C. overnight, then is cooled and is unloaded to afford 222.95 g of a liquid. The liquid is mixed with 0.31 mL of acetic acid to neutralize the potassium hydroxide catalyst.

Example 7: Alkoxylation of C8-C10 Alcohols: C8-C10+5PO+7EO

The 2 L Parr reactor is charged with 50.09 g (349 mmol) of the C8-C10 alcohol mixture of Preparation 2 containing 0.61 wt. % KOH. After a pressure check and series of nitrogen purges, the mixture is warmed to 130° C. for the addition of 101.5 g (1748 mmol) of propylene oxide at an addition rate of 1 g/min. After the addition is complete and the pressure stabilizes, 107.4 g (2438 mmol) of ethylene oxide is added at a rate of 1 g/min. The reaction product is held at 130° C. overnight, then is cooled and is unloaded to afford 252.07 g of a liquid. The liquid is mixed with 0.31 mL of acetic acid to neutralize the potassium hydroxide catalyst.

Example 8: Alkoxylation of C8-C10 Alcohols: C8-C10+5PO+9EO

The 2 L Parr reactor is charged with 50.25 g (350 mmol) of the C8-C10 alcohol mixture of Preparation 2 containing 0.61 wt. % KOH. After a pressure check and series of nitrogen purges, the mixture is warmed to 130° C. for the addition of 101.2 g (1742 mmol) of propylene oxide at an addition rate of 1 g/min. After the addition is complete and the pressure stabilizes, 138.4 g (3142 mmol) of ethylene oxide is added at a rate of 1 g/min.

The reaction product is held at 130° C. overnight, then is cooled and is unloaded to afford 283.47 g of a liquid. The liquid is mixed with 0.31 mL of acetic acid to neutralize the potassium hydroxide catalyst.

Example 9: Alkoxylation of C8-C10 Alcohols: C8-C10+5PO+15EO

The 2 L Parr reactor is charged with 50.27 g (350 mmol) of the C8-C10 alcohol mixture of Preparation 2 containing 0.61 wt. % KOH. After a pressure check and series of nitrogen purges, the mixture is warmed to 130° C. for the addition of 101.2 g (1742 mmol) of propylene oxide at an addition rate of 1 g/min. After the addition is complete and the pressure stabilizes, 231.9 g (5264 mmol) of ethylene oxide is added at a rate of 1 g/min. The reaction product is held at 130° C. overnight, then is cooled and is unloaded to afford 357.38 g of a liquid. The liquid is mixed with 0.31 mL of acetic acid to neutralize the potassium hydroxide catalyst.

Comparative Experiments A and B (not Embodiments of this Disclosure)

Two surfactants based upon 2-EH, namely 2-EH+5PO+7EO and 2-EH+5PO+9EO, are prepared following procedures similar to that of Example 2.

Surfactant Properties

The C8-C10 alkoxylate surfactant samples are first assessed by cloud point according to ASTM D2024-09 for a one wt. % solution of surfactant in deionized water using a Mettler Toledo FP900 ThermalSystem with an FP90 central processor and FP81 measuring cell. Cloud points are also measured for 10 wt. % solutions of surfactants in a 1:3 butyl carbitol/deionized water mixture. Surface tension and critical micelle concentration (CMC) of the samples are obtained on a KRÜSS Tensiometer K-100 using a Wilhelmy plate at 25° C. in water. Surface tension change with concentration is measured by incrementally adding a surfactant to deionized water, and CMC values are determined using KRÜSS LabDesk Software for Force Tensiometer K100. The results are summarized in Table 2.

TABLE 2

Cloud point, surface tension, and CMC of surfactant samples

| Sample | Cloud point (° C.) 1 wt. % | Cloud Point (° C.) 10 wt. % in 1:3 butyl carbitol/ water solution | Surface Tension mN/m | CMC ppm |
| --- | --- | --- | --- | --- |
| C8-C10 + 3PO + 3EO | n.s. | 52 | 28 | 263 |
| C8-C10 + 3PO + 6EO | 45 | 62 | 28 | 552 |
| C8-C10 + 3PO + 9EO | 53 | 71 | 28 | 593 |
| C8-C10 + 5PO + 5EO | 15 | 60 | 29 | 237 |
| C8-C10 + 5PO + 7EO | 62 | 67 | 29 | 361 |
| C8-C10 + 5PO + 9EO | n.m. | 72 | 29 | 542 |
| 2-EH + 5PO + 6EO | 40 | n.m. | 30 | 914 |
| 2-EH + 5PO + 9EO | 61 | n.m. | 31 | 1066 |
| Lutensol XP 50 | n.s. | 60 | 28 | 753 |
| Lutensol XP 60 | n.s. | 67 | 27 | 877 |
| Lutensol XP 70 | n.s. | 71 | 27 | 892 | n.m. = not measured
n.s. = not soluble or not fully soluble at room temp.

As seen from the data in Table 2, the two comparative 2-EH based surfactants, namely 2-EH+5PO+7EO and 2-EH+5PO+9EO, exhibit high CMC values, 914 ppm and 1066 ppm, respectively. The C8-C10 alkoxylate surfactant samples, C8-C10+3PO+6EO and C8-C10+3PO+9EO exhibit lower CMC values, which are in the range of 550-600 ppm. C8-C10+5PO+5EO and C8-C10+5PO+7EO demonstrate even lower CMC values in the range of 230-370 ppm.

LUTENSOL series surfactants are ethoxylated 2-PH materials that are commercially available from BASF. LUTENSOL XP 50 and C8-C10+5PO+5EO have the same cloud point of 6° C. in a 1:3 butyl carbitol/water mixture. The CMC value of LUTENSOL 50, 753 ppm, is significantly higher than that of C8-C10+5PO+5EO (237 ppm). The same phenomenon can be seen by comparing LUTENSOL XP 60 with C8-C10+5PO+7EO. The CMC of LUTENSOL XP 60 at 877 ppm is higher than the CMC of C8-C10+5PO+7EO at 361 ppm, while these two surfactants show the same cloud point in a 1:3 butyl carbitol/water mixture. The same conclusion can be drawn by comparing LUTENSOL XP 70 with C8-C10+3P0+9EO. These results indicate that the C8-C10 alkoxylate surfactants have lower CMC values than comparable 2-PH based LUTENSOL XP surfactants.

Biodegradable Study of C8-C10 Alkoxylates

The ready biodegradability of three surfactants, namely C8-C10+3PO, C8-C10+3PO+6EO, and C8-C10+3PO+9EO, is evaluated according to OECD Guideline No. 301F: Manometric Respirometry Test. Biodegradation is evaluated in duplicate reaction mixtures containing a defined mineral medium that is inoculated with activated sludge biosolids (30 mg/L dry wt.) from the City of Midland, Mich., USA, wastewater treatment plant. The test materials are coated onto a granular silica gel substrate (20 wt. % loading) and are tested at a concentration of approximately 20 mg/L, giving a theoretical oxygen demand (ThOD) of approximately 50 mg/L. Biodegradation of a reference substance (aniline) is also measured in duplicate to evaluate the viability of the inoculum and to determine precision in the respiration measurements. Oxygen consumption in the continuously-stirred (22° C.) reaction mixtures is measured at 6 hr intervals over the 28 day test period using a respirometer. Respiration in the biodegradation reactions is corrected for that occurring in inoculum blanks containing only the inoculated mineral medium, and this net respiration is compared to the ThOD for each substance to determine percent biodegraded material (BD) based on oxygen consumption (DO2). The time for onset of biodegradation (biodegradability to exceed 10% DO2) for the three experimental surfactants ranges from 3.1 to 3.6 days, whereas the time to exceed the pass level (60% DO2) ranges from 7.6 to 12.9 days. Each of the three substances meets the pass level and 10-day window criteria for classification as "readily biodegradable." The results of this test meet each of the OECD-specified criteria for determining validity, as related to inoculum viability, control of incubation temperature and pH, and precision among replicate test mixtures. Therefore, the results and associated conclusions of this test can be considered as valid and reliable, showing that each of these surfactants meets current OECD criteria for classification as "readily biodegradable" and, by definition, are expected to rapidly and ultimately biodegrade in a variety of aerobic environments. The testing results are summarized in Table 3a.

TABLE 3a

OECD 301F Ready Biodegradability Test Results (1$^{st}$ batch run)

| Reaction Mixtures | Time to Achieve (Days) | | BD (%) at | |
| --- | --- | --- | --- | --- |
| | 10% BD | 60% BD | 10-d Window | Day 28 |
| Positive Controls | 3.0 | 5.1 | 115 ± 20 | 137 ± 4 |
| C8-C10 alcohol + 3PO + 9EO | 3.6 | 11.6 | 67.3 ± 5.1 | 94.2 ± 14 |
| C8-C10 alcohol + 3PO + 6EO | 3.1 | 12.9 | 61.7 ± 0.5 | 88.8 ± 0.7 |
| C8-C10 alcohol + 3PO | 3.6 | 7.6 | 86.4 ± 2.7 | 99.9 ± 4.6 |

In a second batch run, three surfactants, namely C8-C10+5PO, C8-C10+5PO+9EO, and 2-EH+5PO+9EO, are evaluated according to OECD Guideline No. 301F. The C8-C10+5PO and C8-C10+5PO+9EO samples reach over 60 percent of biodegradability in the 28 day-window criteria for classification as "readily biodegradable." The testing results are summarized in Table 3b.

TABLE 3b

OECD 301F Ready Biodegradability Test Results (second bath run)

| Reaction Mixtures | Time to Achieve (Days) | | BD at | |
| --- | --- | --- | --- | --- |
| | 10% BD | 60% BD | 10-d Window | Day 28 |
| Positive Controls | 1.0 | 3.0 | 81.0 ± 0.9 | 90.4 ± 3.1 |
| C8-C10 + 5PO | 4.8 | 19.8 | 48.5 ± 6.0 | 66.9 ± 8.3 |
| C8-C10 + 5PO + 9EO | 5.5 | 21.0 | 43.7 ± 2.7 | 65.7 ± 5.8 |
| 2-EH + 5PO + 6EO | 5.0 | 19.3 | 51.9 ± 0.4 | 64.8 ± 1.4 |

Gel Range

In the use of surfactants in aqueous solutions, a wide gel range would cause handling and operation difficulties. A narrow gel range is highly desirable in order to avoid handling and operation problems in formulation. Flowability and gel formation of aqueous solutions of C8-C10+5PO+5EO, C8-C10+5PO+7EO, and C8-C10+5PO+9EO samples are tested in the concentration range of 10 wt. % to 90 wt. % at three different temperatures (room temperature, 60° C. and 15° C.). All three surfactants demonstrate very narrow gel ranges, similar to 2-EH+5PO+6EO and significantly better than conventional ethoxylate surfactants. The testing results are summarized in Table 4.

TABLE 4

The measurement of gel range for surfactants of this disclosure

| | Sample | | | | | | | | | | |
|---|---|---|---|---|---|---|---|---|---|---|---|
| | C8-C10 alcohol + 5PO + 5EO | | | C8-C10 alcohol + 5PO + 7EO | | | C8-C10 alcohol + 5PO + 9EO | | | 2-EH + 5PO + 6EO | C12-C15-7EO | NP-9 |
| | Temperature (° C.) | | | | | | | | | | | |
| weight % | RT | 60 C. | 15 C. | RT | 60 C. | 15 C. | RT | 60 C. | 15 C. | RT | RT | RT |
| 10% | IL | L | L | L | L | L | L | L | L | L | L | L |
| 20% | IL | L | L | L | L | L | L | L | L | L | L | L |
| 30% | IL | L | L | L | L | L | L | L | L | L | G | L |
| 40% | IL | L | L | L | L | L | L | L | L | L | G | L |
| 50% | L | L | L | L | L | L | L | L | L | L | G | G |
| 60% | G | L | G | TL | TL | TL | L | TL | L | G | G | G |
| 70% | L | L | G | G | G | G | G | G | G | G | G | G |
| 80% | L | L | L | L | L | L | L | L | L | L | L | L |
| 90% | L | L | L | L | L | L | L | L | L | L | L | L |

G means gel; L means liquid; TL means thick liquid; IL means two insoluble phases. C12-C15-7EO is linear C12-C15 alcohol ethoxylated with 7 EO; NP-9 is TERGITOL ™ NP-9 surfactant, nonylphenol ethoxylated with 9 EO.

Dissolution Time

When a surfactant is added to water or an aqueous solution to make a formulation, it is highly desirable that the surfactant can be rapidly dissolved to form a homogeneous solution under a common agitation condition. The dissolution time of the C8-C10 PO/EO alkoxylate surfactants to form a 10 wt. % aqueous solution (50 grams of the surfactant in 500 ml de-ionized water) at room temperature under 800 rpm magnetic stirring is measured in a 1000 ml beaker and the results are summarized in Table 5.

TABLE 5

Dissolution time

| Sample | Dissolution time (sec) |
|---|---|
| C8-C10 + 3PO + 6EO | 79.6 |
| C8-C10 + 3PO + 9EO | 14.0 |
| C8-C10 + 5PO + 5EO | N/A |
| C8-C10 + 5PO + 7EO | 64.7 |
| C8-C10 + 5PO + 9EO | 37.1 |
| 2-EH + 5PO + 6EO | 231.0 |
| C12-C15 – 7EO | >3600 |
| TERGITOL NP-9 | >3600 |

N/A= When adding C8-C10 + 5PO + 5EO to water, solution appears milky, so the dissolution time cannot be determined.

As seen in Table 5, all C8-C10 PO/EO alkoxylate surfactants can be dissolved in water in less than 80 seconds, which is significantly quicker than the conventional ethoxylated alcohol surfactants and also 2-EH+5PO+6EO. Rapid dissolution makes a surfactant much easier to use.

Hard Surface Cleaning Application

Removal of oily soil from hard surfaces, such as vinyl tiles, can be facilitated by a surfactant. A conventional industry test to evaluate hard surface cleaning efficiency is the Gardner scrub test (ASTM D-2486). A high throughput hard surface cleaning efficiency test following the ASTM D-2486 method is used to evaluate the hard surface cleaning efficiency of the surfactants. The level of cleaning is determined by the gray value or the scrubbed spot after the scrubbing. The larger the gray value, the whiter the scrubbed spot is and the better the cleaning efficiency.

Formulations are prepared based on the recipe of a generic hard surface cleaning formulation A (Table 6), and are then visually observed for stability and are tested with the scrubbing test.

TABLE 6

| Generic formulation A (wt. %) | |
|---|---|
| Surfactant | 1 |
| DOWANOL PnB | 3 |
| Monoethanolamine (MEA) | 0.5 |
| DI Water | 95.5 |
| Totals | 100 |

Full results, organized as ΔL change, are summarized in Table 7.

TABLE 7

A summary of hard surface cleaning test.

| Surfactant in generic formulation A | | ΔL |
|---|---|---|
| 2-EH + 5PO + 6EO | Average | 55.69 |
| | St. Dev. | 6.37 |
| deionized water only | Average | 18.16 |
| | St. Dev. | 1.63 |
| C8-C10 + 3PO + 6EO | Average | 51.78 |
| | St. Dev. | 11.76 |
| nil surfactant | Average | 26.07 |
| | St. Dev. | 1.28 |

For hard surface cleaning applications, 2-EH+5PO+6EO is the conventional benchmark, as it has demonstrated outstanding hard surface cleaning efficiency in comparison with other commercial surfactant products; see US 2011/0098492A. A larger cleaning difference (ΔL) value translates to greater cleaning efficiency. The cleaning results indicate that C8-C10+3PO+6EO has cleaning performance comparable to that of 2-EH+5PO+6EO. Thus, the C8-C10 alkoxylates are good as hard surface cleaning agents.

What is claimed is:

1. An alkoxylate mixture comprising compounds of the following formula:

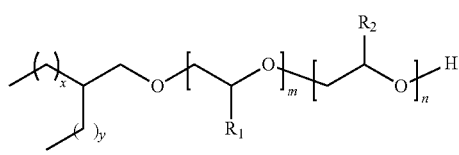

wherein R1 is either methyl or ethyl or a combination thereof, R2 is either hydrogen, methyl or ethyl or any combination thereof, wherein x is 3 or 4, y is 1 or 2, m has an average value of from 1 to 15, and n has an average value of 0 to 40, with the proviso that the mixture includes a compound wherein x+y is 4, a compound wherein x+y is 5 and a compound wherein x+y is 6, wherein the alkoxylate mixture comprises 10 to 40 mole percent of compounds with x+y=4, 20 to 80 mole percent of compounds with x+y=5, and 10 to 40 mole percent of compounds with x+y=6, wherein a total mole percent is 100.

2. An alkoxylate mixture of claim 1 wherein R2 is hydrogen or methyl, x is 3 or 4, y is 1 or 2, and m has an average value of from 1 to 15.

3. An alkoxylate mixtures of claim 1 wherein R1 is methyl, x is 3 or 4, y is 1 or 2, and m has an average value of from 3 to 5.

4. An alkoxylate mixture of claim 1 wherein R1 is methyl, R2 is hydrogen, x is 3 or 4, y is 1 or 2, m has an average value of from 3 to 5, and n has an average value of 3 to 15.

5. An alkoxylate mixture of claim 1 wherein m is from 3 to 5 and n is from 3 to 40.

6. An alkoxylate mixture of claim 1 wherein m is 3 to 10, and n is from 1 to 40.

7. An alkoxylate mixture of claim 1 comprising 20 to 30 mole percent of compounds with x+y=4, 40 to 60 mole percent of compounds with x+y=5, and 20 to 30 mole percent of compounds with x+y=6, wherein the total mole percent is 100.

8. A cleaning composition comprising a mixture of claim 1.

9. An alkoxylate mixture of claim 1 prepared by a process comprising the following steps, (1) conducting a cross aldol condensation of a mixture of butyraldehyde and valeraldehyde under reaction conditions sufficient to produce a corresponding mixture of enals; (2) hydrogenating the mixture of enals under reaction conditions sufficient to produce a mixture of alcohols; and (3) alkoxylating the mixture of alcohols in one or more stages under reaction conditions sufficient to produce the alkoxylate mixture.

* * * * *